United States Patent
Barnett et al.

(10) Patent No.: US 6,772,157 B2
(45) Date of Patent: Aug. 3, 2004

(54) DELEGATED ADMINISTRATION OF INFORMATION IN A DATABASE DIRECTORY

(75) Inventors: Janet Arlie Barnett, Pattersonville, NY (US); Barbara Jean Vivier, Niskayuna, NY (US); Kareem Sherif Aggour, Schenectady, NY (US); Mark Mitchell Kornfein, Latham, NY (US)

(73) Assignee: General Electric Company, Niskayuna, NY (US)

( * ) Notice: Subject to any disclaimer, the term of this patent is extended or adjusted under 35 U.S.C. 154(b) by 414 days.

(21) Appl. No.: 09/761,000

(22) Filed: Jan. 16, 2001

(65) Prior Publication Data

US 2002/0095414 A1 Jul. 18, 2002

Related U.S. Application Data

(60) Provisional application No. 60/241,645, filed on Oct. 19, 2000.

(51) Int. Cl.[7] .............................................. G06F 17/30
(52) U.S. Cl. ............................. 707/9; 707/10; 709/206; 709/229; 709/246; 713/201
(58) Field of Search .............................. 707/10, 3, 101, 707/9, 103; 709/217, 218, 227, 229, 206, 246; 713/201

(56) References Cited

U.S. PATENT DOCUMENTS 5,671,360 A * 9/1997 Hambrick et al. ............. 705/9
6,073,242 A * 6/2000 Hardy et al. ................ 713/201
6,088,451 A 7/2000 He et al.
6,144,959 A 11/2000 Anderson et al.
6,408,336 B1 * 6/2002 Schneider et al. .......... 709/229

OTHER PUBLICATIONS

Oblix NetPoint 4.0 [online]. Oblix, Inc. [retrieved on Dec. 18, 2000]. Retrieved from the Internet:<URL: http://www.oblix.com/products_and_solutions/netpoint/>.
Securant Products [online]. Securant Technologies [retrieved on Dec. 18, 2000]. Retrieved from the Internet: <URL: http://www.securant.com/ie/main_products.html>.
Delegated Management Services [online]. Netegrity, Inc. [retrieved on Dec. 18, 2000]. Retrieved from the Internet: <URL: http://www.netegrity.com/products/dms.html>.
iPlanet Delegated Administrator 4.5 Datasheet [online]. iPlanet International [retrieved on Dec. 18, 2000]. Retrieved from the Internet:<URL: http://iplanet.com/products/infrastructure/dir_security/del_admin/>.

* cited by examiner

*Primary Examiner*—Jean M. Corrielus
(74) *Attorney, Agent, or Firm*—David C. Goldman; Patrick K. Patonode

(57) ABSTRACT

A delegated administration tool for administrating information in a database directory. The delegated administration tool enables an administrator to delegate administration and various types of administrative authority to other users within a community of users. In particular, an administrator with proper authority may create new administrative domains and assign authority referred to as delegation authority and edit authority to other users. The creation of additional administrative domains and the assignment of the delegation authority and edit authority can continue to an arbitrary level within the community.

48 Claims, 17 Drawing Sheets

FIG. 14a

Add/Edit Admin Profile

Admin Profile Data:

Note that the Admin Profile ID must contain the string "admin" in it. This ID is case-insensitive, so it may contain "Admin", etc.

Domain Name: ▶ WebProfileAdmin
Description: ▶ User's Web Profile Administrator

Editable Attributes: facsimiletelephonenumber
gemsadminrole
gemsatgkey
gemscrmkey Managed Role Groups: GEMS Employee
Hospital Employee Managed Offering Groups: AssetMed
Catalog
InstallPro Once you click 'Submit' you will then be taken to a page to create the query rule to define the user group this administrator profile can manage.

Back

Privacy Policy | Terms and Conditions © 1997-2000 General Electric Company

Assign Adminiiistrative and/or Deleggation Authority

Authority of User Kareem S. Aggour:

| Assigned? | Domain | Authority | Expiration |
|---|---|---|---|
| | | | Expires at Midnight on: |
| Yes | CatalogAdmin | Edit | June 18 2004 |
| | | | Never Expires: |
| Yes | CenterAdmin | Delegation | January 1 2000 |
| | | | Never Expires: |
| No | -SelectProfile- | -Select Role- | January 1 2000 |
| | | | Never Expires: |
| No | -SelectProfile- | -Select Role- | January 1 2000 |
| | | | Never Expires: |
| No | -SelectProfile- | -Select Role- | January 1 2000 |

[Add Rows] [Administer Profiles]

(Back) [Reset] [Submit]

FIG. 14c

DELEGATED ADMINISTRATION OF INFORMATION IN A DATABASE DIRECTORY

CROSS REFERENCE TO RELATED APPLICATIONS

This application claims the benefit of U.S. Provisional Application Serial No. 60/241,645 filed on Oct. 19, 2000, and entitled "Approach And Design For Software To Facilitate Delegated Administration Of Information In A Database Directory," which is incorporated by reference herein in its entirety.

BACKGROUND OF THE INVENTION

This disclosure relates generally to community-based computer services and more particularly to administration of community-based computer services.

Generally, a community is a group of people who typically share a common interest. With the advent of the Internet and e-commerce, many companies are forming communities through intranets and extranets, for employees, suppliers, partners and clients. The communities make it easier and less expensive for the employees, suppliers, partners and clients to work together. In the context of computer services, these people are known as computer users or simply users. Information on each of the users in the communities is stored in a broad range of directories and databases. The information may comprise the user's name, location, telephone number, organization, login identification, password, etc. Other information may comprise the user's access privileges to resources such as applications and content. The directories may also store information on the physical devices (e.g., personal computers, servers, printers, routers, communication servers, etc.) in the networks that support the communities. Additional information may comprise the services (e.g., operating systems, applications, shared-file systems, print queues, etc.) available to each of the physical devices. All of the above information is generally known as community-based computer services.

The administration (i.e., the creation, maintenance, modification, updating and disabling) of these community-based computer services becomes difficult as the communities grow in size and complexity. In many cases, administration becomes an almost impossible task, unless a community is sub-divided into more manageable sub-communities. With the creation of these sub-communities, it becomes desirable to use a team of administrators who share responsibilities for administrating the community by assigning different individuals to administer the sub-communities. This type of administration is referred to as delegated administration.

Currently available administration tools that facilitate delegated administration do have their drawbacks. For instance, many limit the ability to delegate to arbitrary levels. In most tools, delegation of authority results in the delegates having unrestricted capabilities. Finally, most tools do not provide the ability to identify an arbitrary set of users whose management is to be delegated.

Therefore, there is a need for an innovative approach that will facilitate delegated administration of community-based computer services so that arbitrary levels of delegation are possible within administration of a community so that delegation can be performed for any type of organization or community, regardless of its structure. In addition, there is a need to be able to provide different types of administrative control so that the authority granted to a delegated administrator can be constrained appropriately. Furthermore, there is a need to be able to provide the capability to identify an arbitrary set of users whose management is to be delegated so that administration can be performed for any type of organization or community, regardless of its structure.

BRIEF SUMMARY OF THE INVENTION

In one embodiment of this disclosure, there is a method, system and computer readable medium that stores instructions for instructing a computer system, to provide delegated administration of a user community. In this embodiment, the user community is divided into at least one administrative domain. Administrative privileges are granted to an administrator for the at least one administrative domain, wherein the administrative privileges include at least one of delegation authority and edit authority. The granted administrative privileges can be delegated to another administrator for the at least one administrative domain.

In a second embodiment of this disclosure, there is a system, method and computer readable medium that stores instructions for instructing a computer system, to enable an administrator to control administration of a user community. In this embodiment, information associated with the user community is provided to a user. The administrator is prompted to define at least one administrative domain for the user community. The administrator is also prompted to define administrative privileges for the at least one administrative domain, wherein the administrative privileges include at least one of delegation authority and edit authority. The at least one administrative domain and administrative privileges defined by the administrator are used to control administration of the user community.

In another embodiment, there is a user community administration tool for managing information associated with a user community. In the user community administration tool there is a domain definition component that defines the user community into at least one administrative domain. An administrative privileges component grants administrative privileges for the at least one administrative domain, wherein the administrative privileges include at least one of delegation authority and edit authority. An information management component manages information associated with the at least one administrative domain in accordance with the granted administrative privileges.

In still another embodiment, there is a system for managing information associated with a user community. This system comprises a database directory that contains a plurality of user information. A user community administration tool manages the plurality of user information in the database directory. The user community administration tool comprises a domain definition component that defines the user community into at least one administrative domain. An administrative privileges component grants administrative privileges for the at least one administrative domain, wherein the administrative privileges include at least one of delegation authority and edit authority. An information management component manages user information associated with the at least one administrative domain in accordance with the granted administrative privileges. A computing unit is configured to serve the user community administration tool and the database directory.

In a further embodiment, there is a system for managing information associated with a user community. This system comprises a database directory that contains a plurality of user information. A user community administration tool manages the plurality of user information in the database directory. The user community administration tool comprises a domain definition component that defines the user community into at least one administrative domain. An administrative privileges component grants administrative privileges for the at least one administrative domain, wherein the administrative privileges include at least one of delegation authority and edit authority. An information management component manages user information associated with the at least one administrative domain in accordance with the delegated administrative privileges. A first computing unit is configured to execute the user community administration tool. A second computing unit is configured to serve the database directory and the user community administration tool to the first computing unit over a network.

BRIEF DESCRIPTION OF THE DRAWINGS

FIGS. 14a–14d show various screen displays that may be presented to a user of the delegated administration tool shown in FIG. 4.

DETAILED DESCRIPTION OF THE INVENTION

Figure 1:
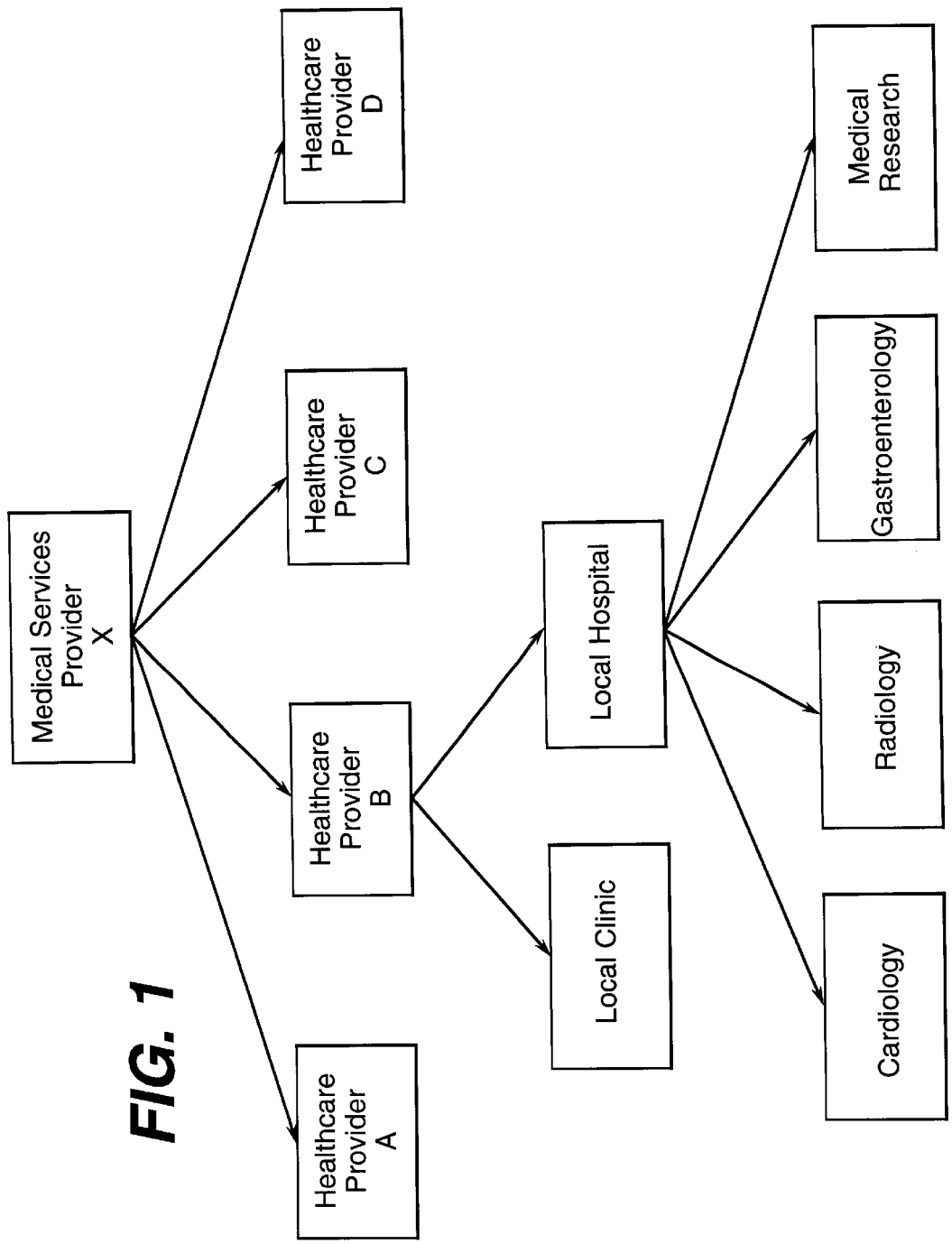
FIG. 1 shows a schematic of an example of a user community.

FIG. 1 shows a schematic of an example of a user community receiving a community of services from a medical services provider. The example shown in FIG. 1 is illustrative of the concept of a user community and is not meant to limit this disclosure. In FIG. 1, Healthcare Providers A–D are communities that receive computer-based services from Medical Services Provider X. Examples of such computer-based services may comprise medical information, the ability to order medical supplies, the ability to schedule patient appointments, the ability to file claims for patient services. Other illustrative examples of computer-based services for this scenario may comprise benchmarking information, healthcare statistics and access to downloadable software. The healthcare providers may also want to provide the computer-based services to their clients, partners, vendors, suppliers, etc. In FIG. 1, Healthcare Provider B provides the computer-based services established from Medical Services Provider X to a Local Clinic and Local Hospital with which it has a relationship. The computer-based services can also be provided to their employees. In FIG. 1, the computer-based services are provided to the various departments in the Local Hospital such as Cardiology, Radiology, Gastroenterology, Medical Research, etc. Similar types of distribution of the computer-based services can be provided for the other healthcare providers (i.e., Healthcare Providers A, C and D).

Medical Services Provider X stores information on each of the users in the community in a database directory. The information may comprise the user's name, location, telephone number, organization, login identification, password, etc. Other information may comprise the user's access privileges to certain resources provided by Medical Services Provider X such as applications and content. The database directory of Medical Services Provider may also store information on the physical devices (e.g., personal computers, servers, printers, routers, communication servers, etc.) in the networks that support the communities. Additional information stored in the database directory may comprise the services (e.g., operating systems, applications, shared-file systems, print queues, etc.) available to each of the physical devices.

Figure 2:
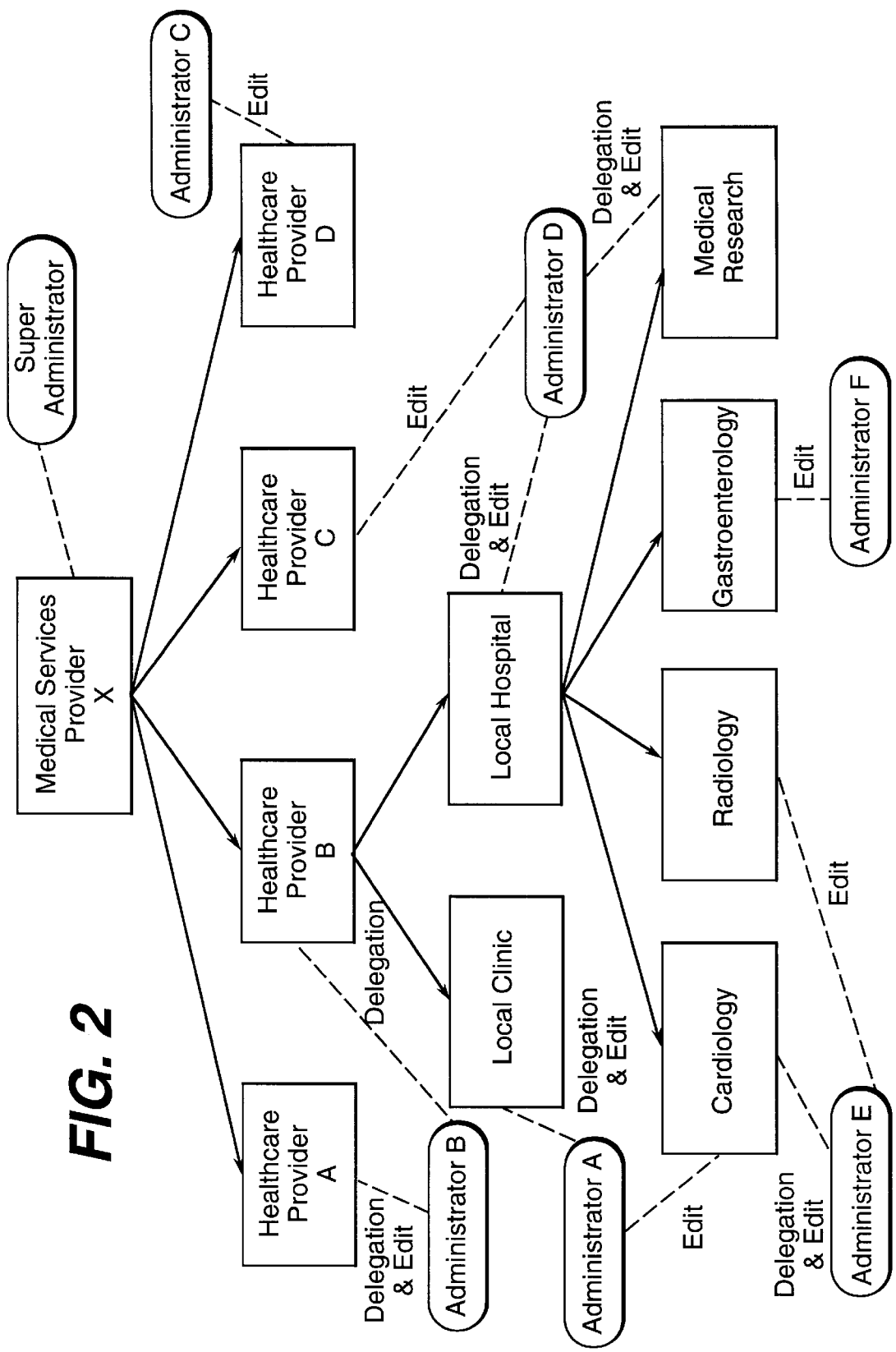
FIG. 2 shows an example of delegated administration of the user community shown in FIG. 1.

Since the user community shown in FIG. 1 can be quite large and complex, it is desirable to subdivide and delegate administration of these communities. FIG. 2 shows an example of delegated administration of the user community shown in FIG. 1. In this example, there is an administrator for each community that is responsible for managing a variety of activities that include but are not limited to modifying user information, updating permissions to certain resources, disabling user accounts, creating user accounts and maintaining user accounts. For instance, the SuperAdministrator manages the activities for Medical Services Provider X; Administrator A manages the activities for the Local Clinic associated with Healthcare Provider B and the Cardiology department of the Local Hospital; Administrator B manages the activities for Healthcare Providers A and B; Administrator C manages the activities for Healthcare Provider D; Administrator D manages the activities for the Local Hospital associated with Healthcare Provider B, the Medical Research departments for the Local Hospital associated with Healthcare Provider B, as well as the activities for Healthcare Provider C; Administrator E manages the activities for the Cardiology and Radiology departments of the Local Hospital associated with Healthcare Provider B; and Administrator F manages the activities for the Gastroenterology department of the Local Hospital associated with Healthcare Provider B. The extent to which Administrators A–F manage activities depends entirely on the type of authority that they have. Below is a more detailed discussion on the various types of authority that an administrator may have. Other forms of delegated administration for this example are possible as will be apparent to people skilled in the art.

For purposes of explaining the delegated administration provided with this disclosure, each block (i.e., Medical Services Provider X, Healthcare Providers AD, Local Clinic, Local Hospital, Cardiology, Radiology, Gastroenterology, Medical Research) in FIG. 2 represents an administrative domain. An administrative domain is a managed object that comprises a set of users, a set of user attributes which can be modified, and a set of allowable values for those data fields over which an administrator has authority. Possible examples of user attributes may include but are not limited to employer, role or job description, resources that permission has been granted to access, address and equipment used. Generally, authority may comprise one of two types: edit authority or delegation authority. An administrator has edit authority within the administrative domain when he or she may edit certain attributes of the users. An administrator has delegation authority within the administrative domain when he or she may define a subset of the users and identify attributes for modification, in order to create an administrative sub-domain. The assignment of the administrative sub-domain to a person is the delegation of that domain. The ability to create an administrative sub-domain and to assign that domain to a user is delegation authority. Although the authority described in this disclosure relates to edit authority and delegation authority, one of ordinary skill in the art will recognize that other types of authority such as view, modify, delete, temporary delegation, as well as similar operations, but with limitations on the extent of viewable data, are possible as well. These examples of authority can be used in addition to, in place of, or in combination with the delegation and edit authority.

As shown in FIG. 2, an administrator may have multiple administrative domains over which he or she has authority (e.g., Administrator A, B, D and E). Also, more than one administrator may have authority over the same administrative domain. For example in FIG. 2, Administrators A and E both have authority over the Cardiology domain, wherein Administrator A has edit authority and Administrator E has both delegation and edit authority. An administrator may have edit authority, delegation authority or both with respect to a given domain.

With regard to the SuperAdministrator, he or she generally has both edit and delegation authority over all domains. Basically, there are no functions that the SuperAdministrator cannot perform. For example, the SuperAdministrator can create, modify or delete anything in the system. Some other functions that the SuperAdministrator can perform include determining which administrators have delegation authority or edit authority over any domain and displaying a list of domains for a specific user.

Referring again to the administrator, below are some other general capabilities that can be performed in this position. One capability is that an administrator cannot assign herself or himself edit or delegation authority if he or she does not already have it. Also, an administrator must select one of his or her authorized domains in which to perform tasks. For an administrator with authority over multiple domains, it is necessary to provide the ability for the administrator to select which domain is active and to switch to a different domain during a single administrative session. Only one domain can be operational or active at a time for an administrator. An administrator can search through his or her active domain to identify users with a certain attribute, for any attributes within the active domain. For example, Administrator C can find all New York State employees of the Healthcare Provider D domain. An administrator can search through his or her active domain to identify users that lack a certain attribute or for any attributes within the active domain. For example, Administrator C can locate all Healthcare Provider D employees who do not have phone numbers. These capabilities are illustrative of just a few of the general capabilities that can be performed with the delegated administration aspects of this disclosure and are not meant to be limiting. One of skill in the art will recognize that these capabilities can be changed, while others can be added or removed.

Below is a more detailed discussion of delegation authority as it can be used in the context of this disclosure. The following description for the delegation authority is illustrative of the general concepts used with the delegated administration provided with this disclosure; however, one of skill in the art will recognize that these concepts can be changed, while others can be added or removed. First, an administrator who has delegation authority over a domain can delegate authority further. In particular, he or she may create a subset of users, user attributes and attribute values known as a sub-domain and assign an administrator over that sub-domain. The subset of users and attributes in the sub-domain is limited to those users, attributes and attribute values within the operational (active) domain over which the administrator has delegation authority. Using FIG. 2 as example, Administrator B can delegate a subset of users, attributes and attribute values of the Healthcare Provider B domain to another administrator if he or she wants to. Such delegation may only be made to an individual that is in the enclosing operational domain, e.g., Healthcare Provider B.

When defining a sub-domain, the administrator may restrict the user attributes that a subordinate administrator may edit. For example, Administrator E, a subordinate administrator, may be allowed to edit a user's title and organizational unit, but not a user's salary in the Radiology department of a local hospital. Another function that can be performed by the delegating administrator when it comes time to define a sub-domain, is that the delegating administrator can define rules or patterns by which sets of users are included or excluded from the sub-domain. For example, the creation of the Radiology domain by Administrator D could have been accomplished by identification of all Local Hospital users in the department equal to Radiology.

An administrator cannot change the nature of the operational domain. More specifically, the administrator may not add or remove attributes from the domain and may not include or exclude users by defining additional rules or patterns. The administrator may, however, perform these operations on any sub-domains that fall within an operational domain over which he or she has delegation authority.

An administrator with delegation authority can also delete any administrative sub-domain within his or her operational domain. Also, an administrator with delegation authority is able to assign delegation authority, edit authority or both to a user within his or her operational domain for a sub-domain of the operational domain. An administrator with delegation authority is also able to remove delegation authority, edit authority or both over a sub-domain of the operational domain for any user within his or her operational domain. An administrator does not have the capability to delegate authority to a user that is outside of the operational domain. Also, an administrator may not delegate authority to himself or herself.

Another option available to an administrator is to assign the delegation or edit authority to another person for a specified time period. Thus, it is possible that an administrator's authority with respect to a domain may expire. This capability allows one to delegate authority to cover vacations and other absences. Note that the time period may also be infinite, to support permanent delegation of authority.

If an administrator only has delegation authority, then he or she may not edit user attributes or add or remove user attributes. This allows, for example, a high-ranking company official to delegate the real administrative tasks to others. Another function that an administrator with delegation authority can perform is that he or she can view a list of all administrators for the sub-domains.

Below is a more detailed discussion of edit authority as it can be used in the context of this disclosure. The following description for the edit authority is illustrative of the general concepts used with the delegated administration provided with this disclosure; however, one of skill in the art will recognize that these concepts can be changed, while others can be added or removed. In this disclosure, an administrator with edit authority may not delegate authority. More specifically, the administrator cannot create an administrative sub-domain nor assign an administrator to any existing domains. Also, an administrator with edit authority can edit user attributes for users within the operational (active) domain. Separating delegation authority from edit authority allows the delegation of administering users without the authority to create domains.

Figure 3:
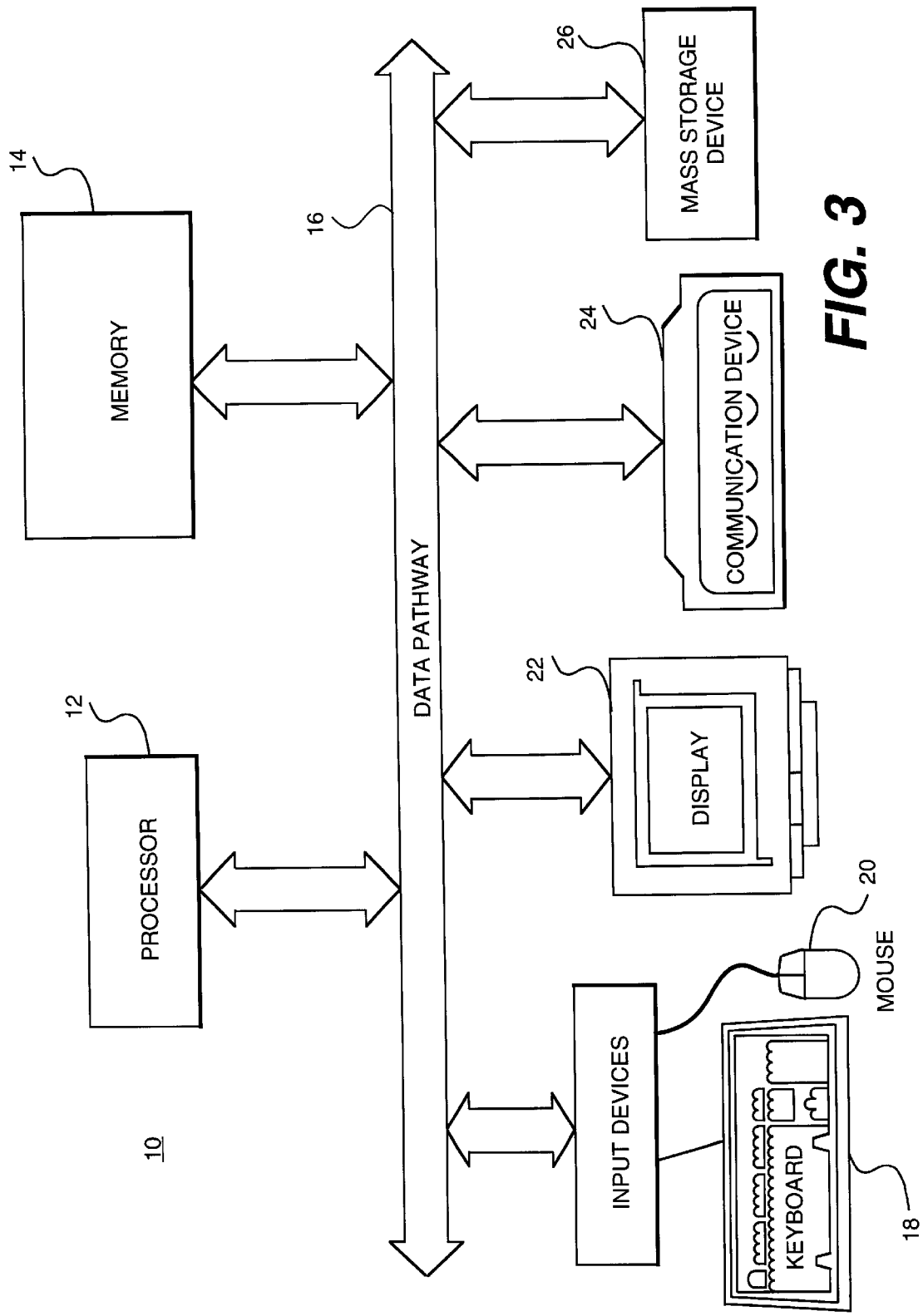
FIG. 3 shows a schematic of a general-purpose computer system in which a delegated administration tool operates.

As an example, the above-described delegated administration capabilities can be implemented in software. FIG. 3 shows a schematic of a general-purpose computer system 10 in which a delegated administration tool operates. The computer system 10 generally comprises at least one processor 12, a memory 14, input/output devices, and data pathways (e.g., buses) 16 connecting the processor, memory and input/output devices. The processor 12 accepts instructions and data from the memory 14 and performs various calculations. The processor 12 includes an arithmetic logic unit (ALU) that performs arithmetic and logical operations and a control unit that extracts instructions from memory 14 and decodes and executes them, calling on the ALU when necessary. The memory 14 generally includes a random-access memory (RAM) and a read-only memory (ROM); however, there may be other types of memory such as programmable read-only memory (PROM), erasable programmable read-only memory (EPROM) and electrically erasable programmable read-only memory (EEPROM). Also, the memory 14 preferably contains an operating system, which executes on the processor 12. The operating system performs basic tasks that include recognizing input, sending output to output devices, keeping track of files and directories and controlling various peripheral devices.

The input/output devices may comprise a keyboard 18 and a mouse 20 that enter data and instructions into the computer system 10. Also, a display 22 may be used to allow a user to see what the computer has accomplished. Other output devices may include a printer, plotter, synthesizer and speakers. A communication device 24 such as a telephone or cable modem or a network card such as an Ethernet adapter, local area network (LAN) adapter, integrated services digital network (ISDN) adapter, or Digital Subscriber Line (DSL) adapter, that enables the computer system 10 to access other computers and resources on a network such as a LAN or a wide area network (WAN). A mass storage device 26 may be used to allow the computer system 10 to permanently retain large amounts of data. The mass storage device may include all types of disk drives such as floppy disks, hard disks and optical disks, as well as tape drives that can read and write data onto a tape that could include digital audio tapes (DAT), digital linear tapes (DLT), or other magnetically coded media. The above-described computer system 10 can take the form of a hand-held digital computer, personal digital assistant computer, notebook computer, personal computer, workstation, mini-computer, mainframe computer or supercomputer.

Figure 4:
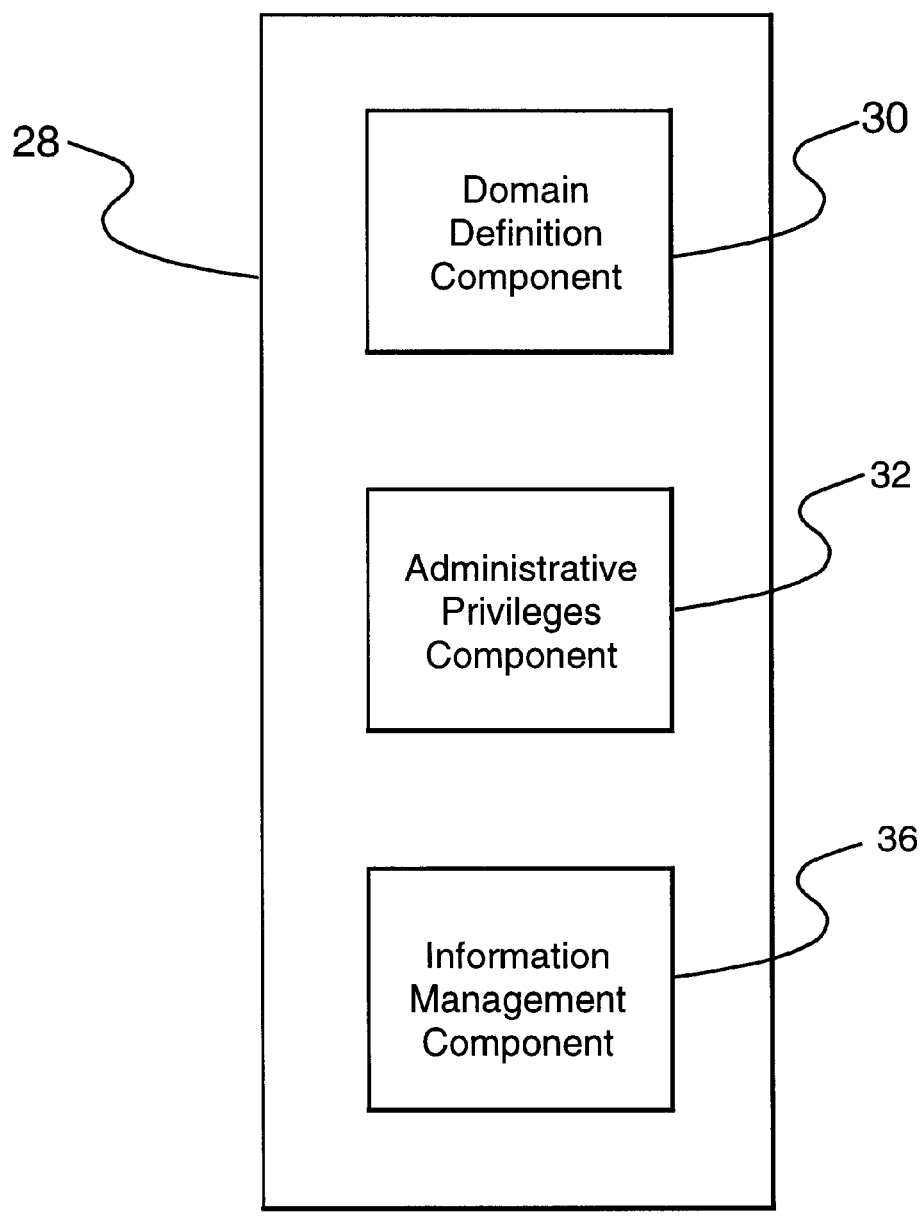
FIG. 4 shows a top-level component architecture diagram of the delegated administration tool that operates on the computer system shown in FIG. 3.

FIG. 4 shows a top-level component architecture diagram of a delegated administration tool 28 that operates on the computer system 10 shown in FIG. 3. The delegated administration tool 28 comprises a domain definition component 30 that enables an administrator to define a user community such as the one shown in FIGS. 1–2 and divide it into at least one administrative domain. As mentioned above, each administrative domain that is defined will include a group of users that form the domain, attributes associated with each of these users and allowable values of these attributes. For example, referring to FIG. 2, the domain definition component 30 permits Administrator E to define the users that form the Radiology domain, as well as the users' attributes and values, which could comprise employer, job description, address, salary, phone number. The delegated administration tool 28 also comprises an administrative privileges component 32. The administrative privileges component 32 enables an administrator to grant administrative privileges for the defined administrative domain in accordance with the above-described manner. The granted administrative privileges may comprise at least one of delegation authority and edit authority. It is also possible to grant other types of authority such as view, modify, delete, temporary delegation, as well as similar operations, but with limitations on the extent of viewable data. These examples of authority can be used in addition to, in place of, or in combination with the delegation and edit authority.

The administrative privileges component 32 also enables an administrator to define which users in the domain will have the granted administrative privileges. More specifically, an administrator can use this component to define various administrators in the domain by assigning delegation authority, edit authority or both types to a particular user. Administrators with delegation authority can also use the domain definition component 30 and administrative privileges component 32 to define sub-domains, define administrative privileges for these domains and define who will have delegation authority, edit authority or both. As long as someone has delegation authority in a particular domain, it is possible to continue to use the domain definition component 30 and administrative privileges component 32 to delegate administration to an arbitrary level within a particular domain. For instance, using FIG. 2 as an example, Administrator E could divide the Cardiology domain into further domains (e.g., doctors and nurses) and assign delegation and edit authority to new administrators. Administrators that are assigned delegation authority can continue to create additional sub-domains (board-certified doctors and nurses trained in specific surgical techniques) and grant authority to other administrators. It is possible to continue to an arbitrary level with respect to the Cardiology domain. However, because Radiology does not have an administrator with delegation authority at that level, Administrator E may only edit it.

The delegated administration tool 28 also comprises an information management component 36 that manages information associated with each of the administrative domains in accordance with the delegated administrative privileges. Depending on the type of authority delegated, an administrator can use the information management component 36 to edit, view or delete specific attributes for a user in a domain. The information management component 36 is not limited to these functions and may perform other functions such as generating reports (e.g., reports on all users within a domain), analyzing data (e.g., determining how frequently some types of data change), performing statistical analysis or allowing users to perform self-administration on certain attributes (e.g., phone number, e-mail address, passwords, etc.).

The delegated administration tool 28 is not limited to a software implementation. For instance, the domain definition component 30, administrative privileges component 32 and the information management component 36 may take the form of hardware or firmware or combinations of software, hardware, and firmware.

In addition, the delegated administration tool 28 is not limited to the domain definition component 30, administrative privileges component 32 and information management component 36. One of ordinary skill in the art will recognize that the delegated administration tool 28 may have other components. For example, the delegated administration tool 28 could also include a workflow component that manages processes surrounding user creation and administration. Also, the delegated administration tool 28 could include a reporting component that reports usage statistics, error conditions, etc. There could also be a transactional management component that performs transactions using 2-phase commit/rollback. Still another component that the delegated administration tool 28 could include is a browsing component for viewing information associated with the hierarchy of administrative domains.

Figure 5:
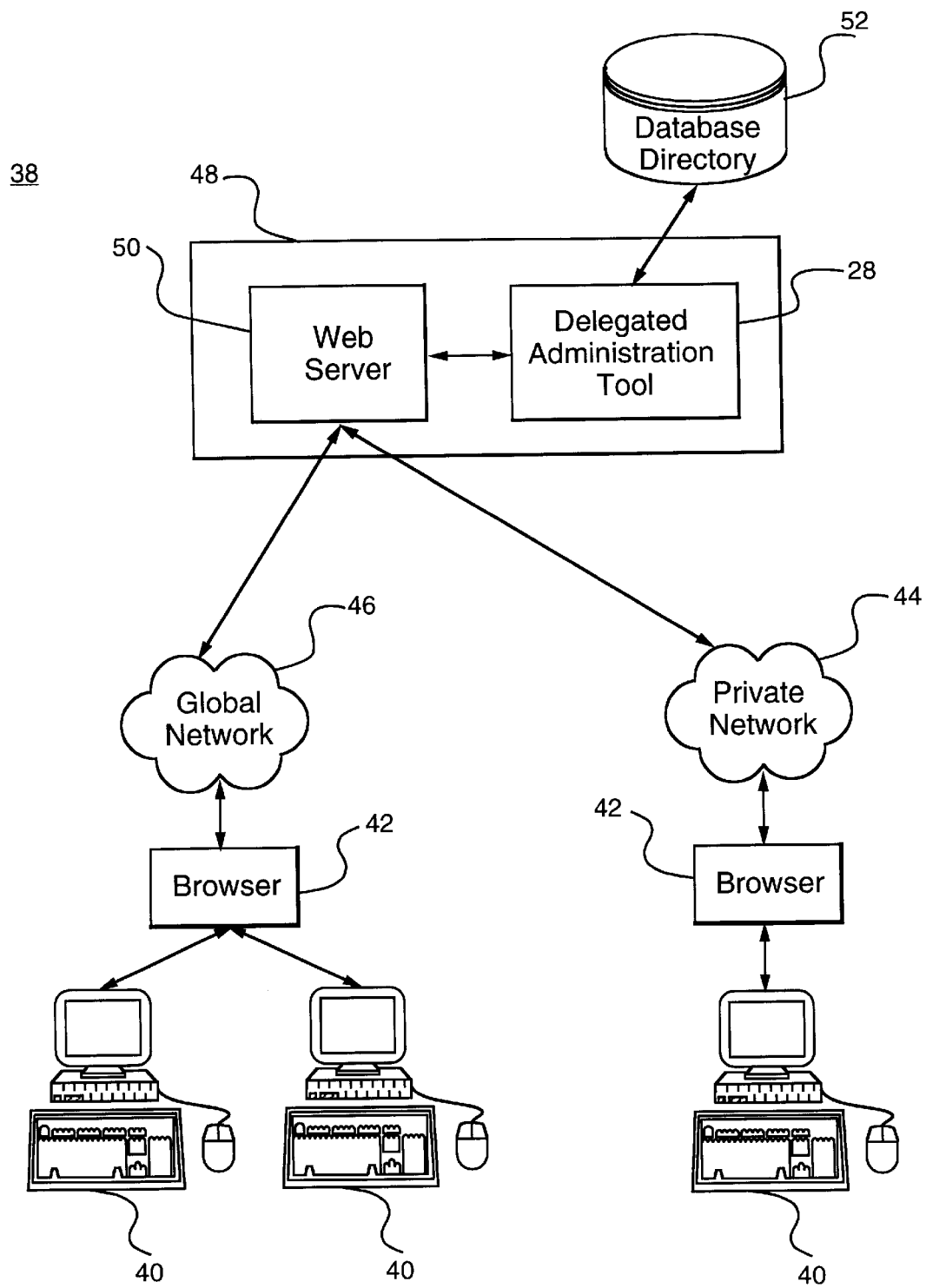
FIG. 5 shows an architectural diagram of a system for implementing the delegated administration tool shown in FIG. 4.

FIG. 5 shows an architectural diagram of a system 38 for implementing the delegated administration tool shown in FIG. 4. FIG. 5 shows that there are several ways of accessing the delegated administration tool 28. A computing unit 40 allows an administrator to access the delegated administration tool 28. As mentioned above, the administrator could be the SuperAdministrator or administrators with delegation authority or edit authority. Also, users in the domain may access the delegated administration tool 28 through a computing unit 40 to perform some basic self-administration. The computing unit 40 can take the form of a hand-held digital computer, personal digital assistant computer, notebook computer, personal computer or workstation. The administrators and users use a web browser 42 such as Microsoft INTERNET EXPLORER or Netscape NAVIGATOR to locate and display the delegated administration tool 28 on the computing unit 40. A communication network such as an electronic or wireless network connects the computing unit 40 to the delegated administration tool 28. FIG. 5 shows that the computing units 40 may connect to the delegated administration tool 28 through a private network 44 such as an extranet or intranet or a global network 46 such as a WAN (e.g., Internet). As shown in FIG. 5, the delegated administration tool 28 resides in a server 48, which comprises a web server 50 that serves the delegated administration tool 28 and a database directory 52 (or directories) that contains the various information for the users in all of the domains that form the community. However, the delegated administration tool does not have to be co-resident with the server 48. If desired, the system 38 may have functionality that enables authentication and access control of users accessing the delegated administration tool 28. Both authentication and access control can be handled at the web server level by the delegated administration tool 28 itself, or by commercially available packages such as Netegrity SITEMINDER.

The information in the database directory 52 as mentioned above may comprise information such as the user's name, location, telephone number, organization, login identification, password, etc. Other information may comprise the user's access privileges to certain resources such as applications and content. The database directory 52 may also store information on the physical devices (e.g., personal computers, servers, printers, routers, communication servers, etc.) in the networks that support the communities. Additional information stored in the database directory 52 may comprise the services (e.g., operating systems, applications, shared-file systems, print queues, etc.) available to each of the physical devices. The database directory 52 can take the form of a lightweight directory access protocol (LDAP) database; however, other directory type databases with other types of schema can be used with the delegated administration tool 28, including relational databases, object-oriented databases, flat files, or other data management systems.

Figure 6:
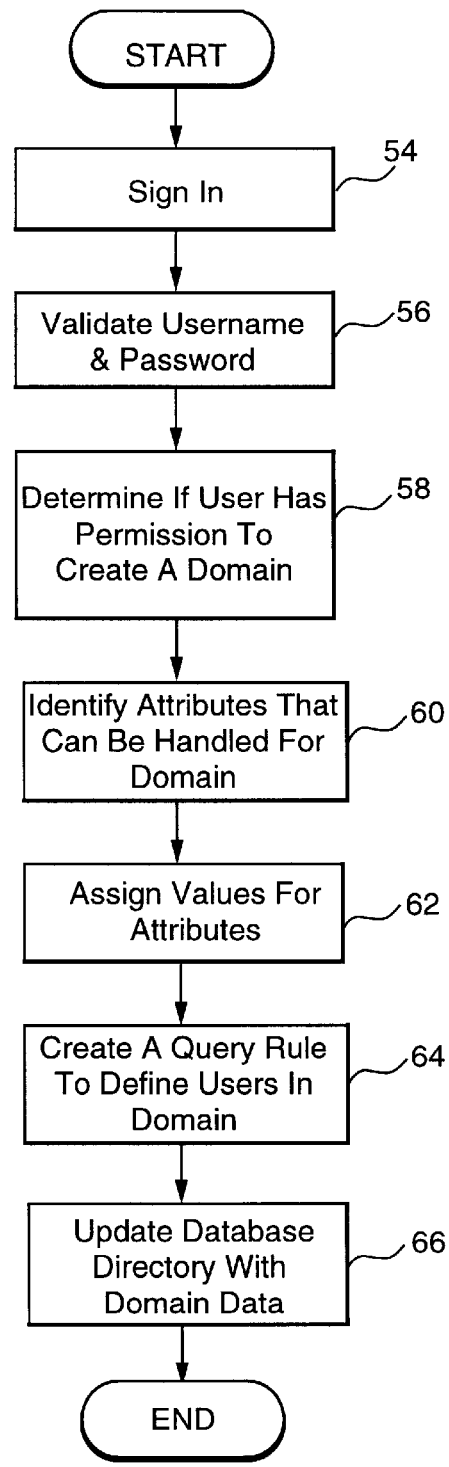
FIG. 6 shows a flow chart of the acts performed to create an administrative domain with the delegated administration tool shown in FIG. 4.

Using the system 38 shown in FIG. 5, an administrator such as a SuperAdministrator or an administrator with delegation or edit authority can use the delegated administration tool 28 to administer a community. Also, users of the community can use the delegated administration tool 28 to perform some self-administration. FIG. 6 shows a flow chart describing the acts performed to create an administrative domain with the delegated administration tool 28. To create an administrative domain, the user must be either a SuperAdministrator or an administrator having delegation authority. At block 54, the SuperAdministrator or administrator with delegation authority signs in. The sign-in act can include entering identity and security information (e.g., a valid username and password). The delegated administration tool validates the username and password at 56. The delegated administration tool then determines if the user has permission (i.e., the user is a SuperAdministrator or administrator with delegation authority) to create an administrative domain at 58. If the user is not authenticated or does not have permission to create an administrative domain, then the user is not allowed to create a domain.

At 60, the user identifies attributes that can be handled for the administrative domain. As mentioned above, attributes comprise any data, which describe information about a user (e.g., employer, job description, resources that permission has been granted to access, address, equipment used, etc.). If desired, some of the attributes can be restricted. For example, a country attribute can be restricted to a limited set of country abbreviations. For instance, in order to represent the countries United States, Canada and Mexico, a set of values can be defined such as USA, CAN or MEX, respectively. For some of these kinds of restricted attributes, it may be desirable to have the restricted attributes appear in the display to the user in the form of a pull-down menu. All of the attributes that are identified can then be viewed, edited or deleted at a subsequent time. At 62, the user assigns allowable values for these identified attributes where needed.

Next, the user constructs a query rule at 64 for defining which users in the community will be in the created administrative domain. Basically, a query rule is a Boolean expression that can be used as a database query, wherein the results of the query define the members of the community or domain. After the query rule has been constructed, the database directory is updated at 66 with the data for the newly created administrative domain. If the SuperAdministrator or administrator with delegation authority wants to create another domain, then blocks 58–66 are repeated.

Otherwise, any time a SuperAdministrator or an administrator with delegation authority desires to create an administrative domain, then blocks 54 through 66 are repeated.

Figure 7:
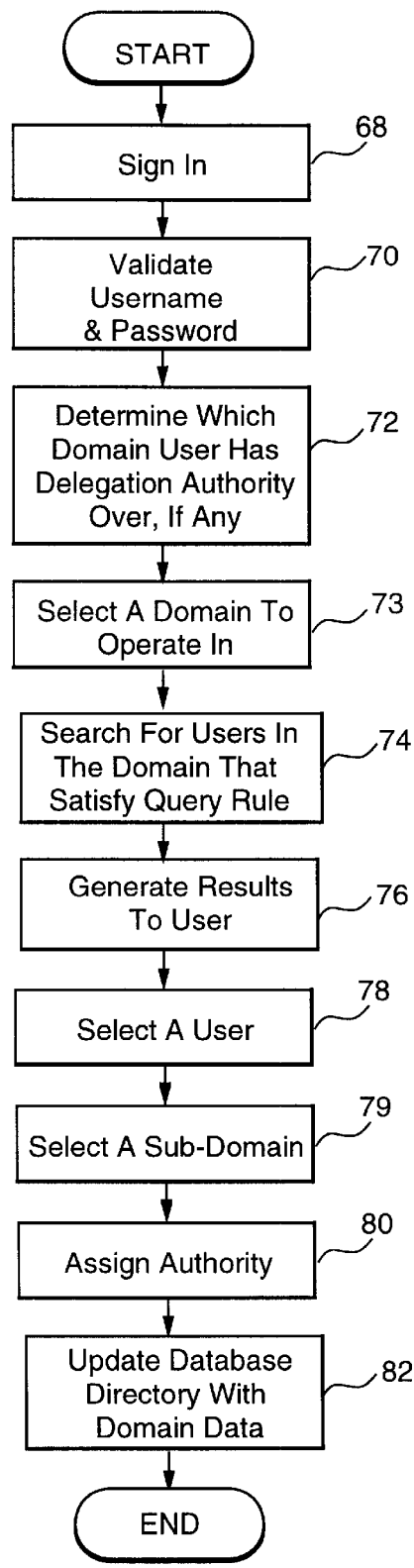
FIG. 7 shows a flow chart describing the acts performed to assign a user delegation authority and/or edit authority for an administrative domain with the delegated administration tool shown in FIG. 4.

FIG. 7 shows a flow chart describing the acts performed to assign a user delegation authority and/or edit authority for a domain. The only users that can assign delegation authority and/or edit authority are either a SuperAdministrator or an administrator having delegation authority. If the SuperAdministrator or administrator having delegation authority has not already logged onto the delegated administration tool, then he or she must sign in at 68. The delegated administration tool validates the username and password at 70. Alternatively, if the SuperAdministrator or administrator having delegation authority has already logged onto the delegated administration tool, then blocks 68–70 may be bypassed. The delegated administration tool determines which domains the user has delegation authority over, if any at 72. Thus, if the user is an administrator with delegation authority, then he or she will have permission to assign delegation authority and/or edit authority for their assigned domains.

At 73, the SuperAdministrator or administrator with delegation authority selects a particular administrative domain to operate in. The SuperAdministrator or administrator with delegation authority may select the administrative domain by inputting the desired domain or a string that describes the domain, or using a combination of both. One of ordinary skill in the art will recognize that there are other input techniques that can be used to select a domain. At 74, the SuperAdministrator or administrator with delegation authority searches for users in the database directory that satisfy search criteria that have been formulated. The delegated administration tool parses and formats the search results and presents the results to the user at 76. The SuperAdministrator or administrator with delegation authority then selects a single user from the results for assigning authority to that person at 78. The SuperAdministrator or administrator with delegation authority then selects a sub-domain of the active domain for which authority will be assigned to that user at 79. Then the SuperAdministrator or administrator with delegation authority selects the type of authority (i.e., delegation authority and/or edit authority) that will be assigned at 80. If desired, the SuperAdministrator or administrator with delegation authority may set an expiration date for the assigned authority. After the authority has been assigned, the database directory is updated at 82 with this data. Thus, any time a SuperAdministrator or an administrator with delegation authority desires to delegate authority of an administrative domain to another user, then at least blocks 73 through 82 are repeated.

Figure 8:
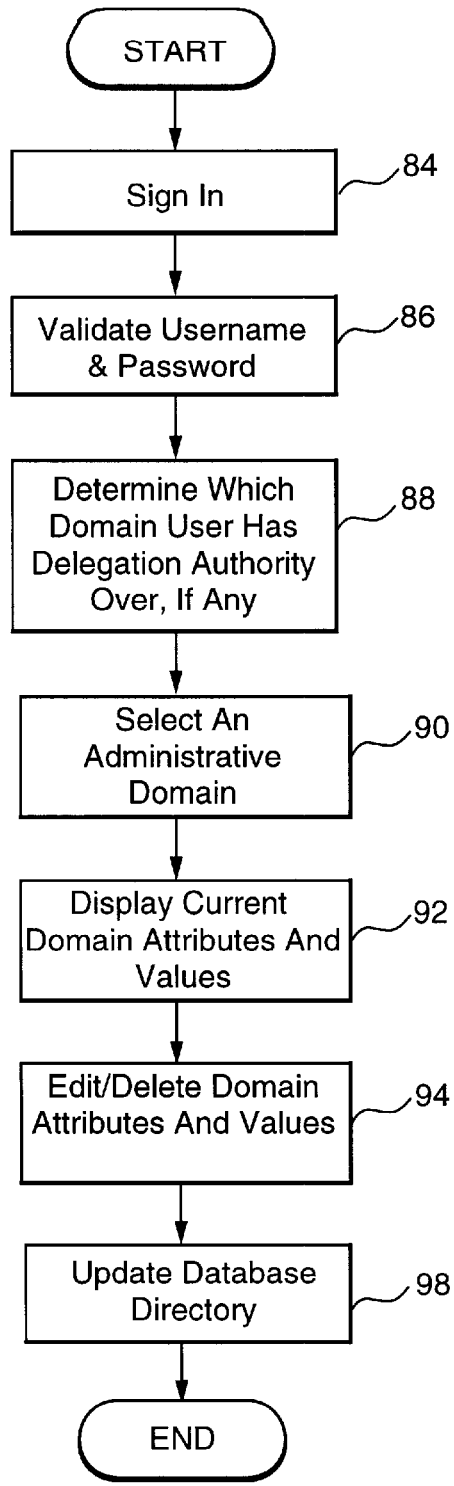
FIG. 8 shows a flow chart describing various acts performed in administering domain parameters with the delegated administration tool shown in FIG. 4.

FIG. 8 shows a flow chart describing various acts performed in administering domain parameters (i.e., attributes and attribute values) associated with an administrative domain. The only users that can administer domain parameters are a SuperAdministrator and an administrator with delegation authority. If the SuperAdministrator or the administrator with delegation authority has not already logged onto the delegated administration tool, then he or she must sign in at 84. The delegated administration tool validates the username and password at 86. Alternatively, if the SuperAdministrator or the administrator with delegation authority has already logged onto the delegated administration tool, then blocks 84–86 may be bypassed. The delegated administration tool determines which domains the user has delegation authority over, if any at 88. Thus, if the user is an administrator with delegation authority then he or she will have permission to administer domain parameters for their assigned domains.

At 90, the SuperAdministrator or administer with delegation authority selects a particular administrative domain to administer. Generally, at this block the SuperAdministrator or administer with delegation authority inputs the domain name and/or a string that describes the domain. The delegated administration tool displays the current attributes and attribute values associated with the domain at 92. The SuperAdministrator or administrator with delegation authority then edits or deletes the domain attributes and attribute values as desired at 94. The delegated administration tool parses and interprets the changes and updates the database directory at 98 with this data.

Figure 9:
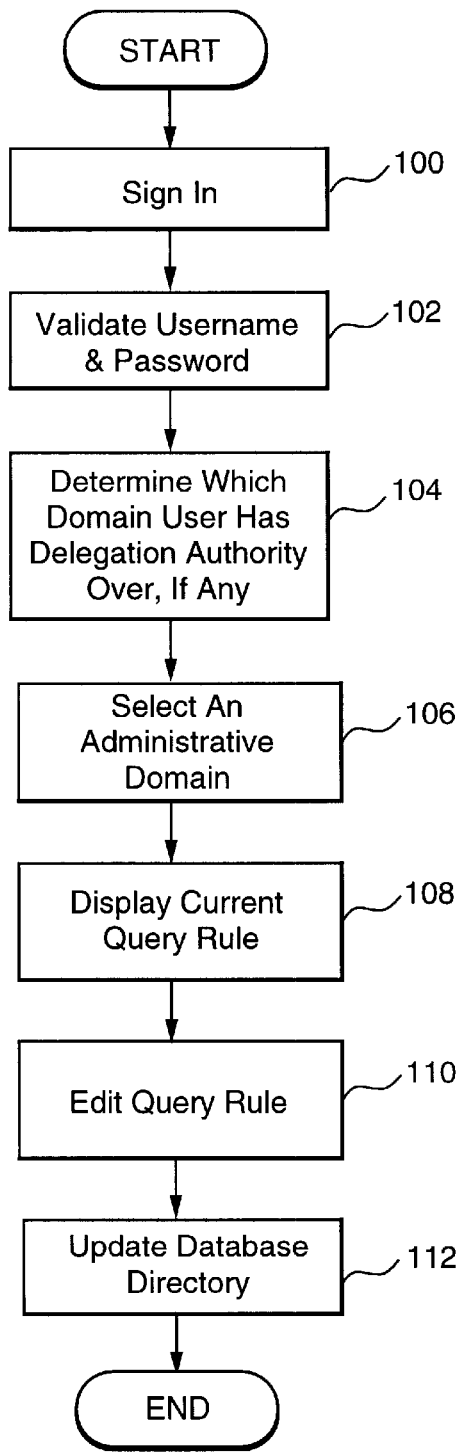
FIG. 9 shows a flow chart describing various acts performed in editing a query rule for an administrative domain with the delegated administration tool shown in FIG. 4.

FIG. 9 shows a flow chart describing various acts performed in editing a query rule associated with an administrative domain. The only users that can edit a query rule for a particular domain are a SuperAdministrator and an administrator with delegation authority in the operational domain that includes the particular domain. If the SuperAdministrator or the administrator with delegation authority has not already logged onto the delegated administration tool, then he or she must sign in at 100. The delegated administration tool validates the username and password at 102. Alternatively, if the SuperAdministrator or the administrator with delegation authority has already logged onto the delegated administration tool, then blocks 100–102 may be bypassed. The delegated administration tool then determines which domains if any that the user has delegation authority over at 104. Thus, if the user is an administrator with delegation authority then he or she will have permission to edit a query rule for any sub-domains of their assigned domains.

At 106, the SuperAdministrator or administer with delegation authority selects a particular administrative domain that contains the query rule that he or she would like to edit and that they have authority to do so. Generally, at this block the SuperAdministrator or administrator with delegation authority inputs the domain name and/or a string that describes the domain. The delegated administration tool displays the current query rule associated with the domain at 108. The SuperAdministrator or administrator with delegation authority then edits the query rule as desired at 110. The delegated administration tool parses and interprets the changes and updates the database directory at 112 with this data.

Figure 10:
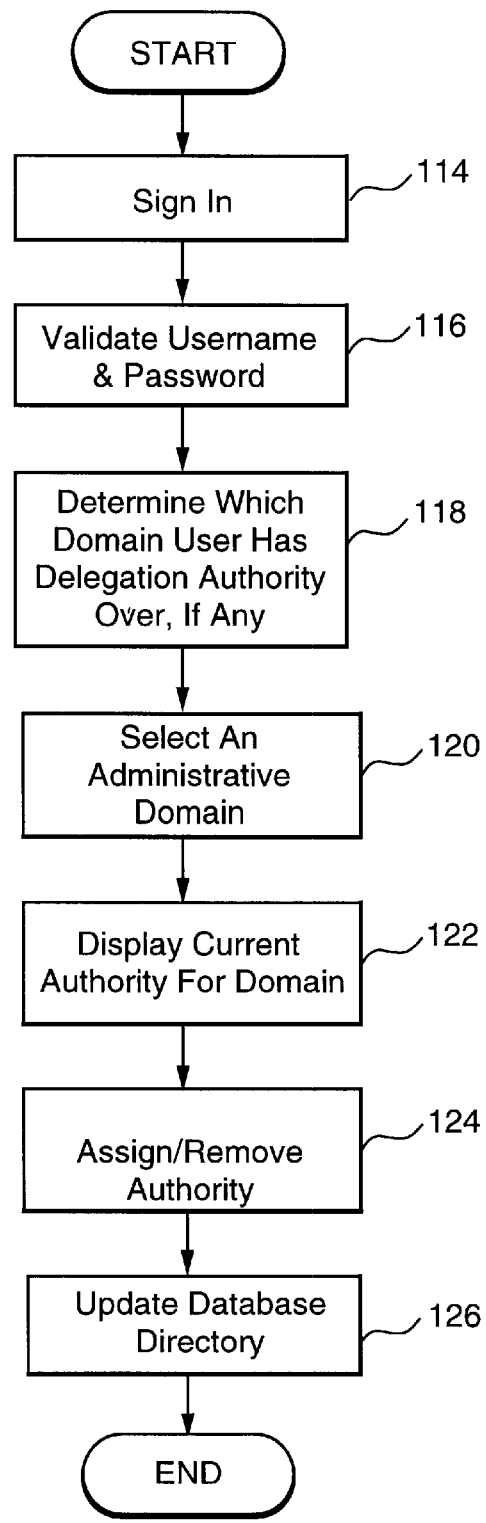
FIG. 10 shows a flow chart describing various acts performed in assigning or removing authority for an administrative domain with the delegated administration tool shown in FIG. 4.

FIG. 10 shows a flow chart describing various acts performed in modifying or deleting the authority assigned to an administrator of an administrative domain. The only users that can modify or delete the authority assigned to an administrator of an administrative domain are a SuperAdministrator and an administrator with delegation authority on that domain. If the SuperAdministrator or the administrator with delegation authority has not already logged onto the delegated administration tool, then he or she must sign in at 114. The delegated administration tool validates the username and password at 116. Alternatively, if the SuperAdministrator or the administrator with delegation authority has already logged onto the delegated administration tool, then blocks 114–116 may be bypassed. The delegated administration tool determines which domains the user has delegation authority over, if any at 118. Thus, if the user is an administrator with delegation authority, then he or she will have permission to modify or delete domain authority for their assigned domains.

At 120, the SuperAdministrator or administer with delegation authority selects a particular administrative domain that he or she would like to edit. Generally, at this block the SuperAdministrator or administer with delegation authority inputs the domain name and/or a string that describes the domain. The delegated administration tool displays the delegated administrator and their authority for the domain at 122. The SuperAdministrator or administrator with delegation authority then modifies or removes the authority from the administrator at 124. The delegated administration tool parses and interprets the changes and updates the database directory at 126 with this data.

Figure 11:
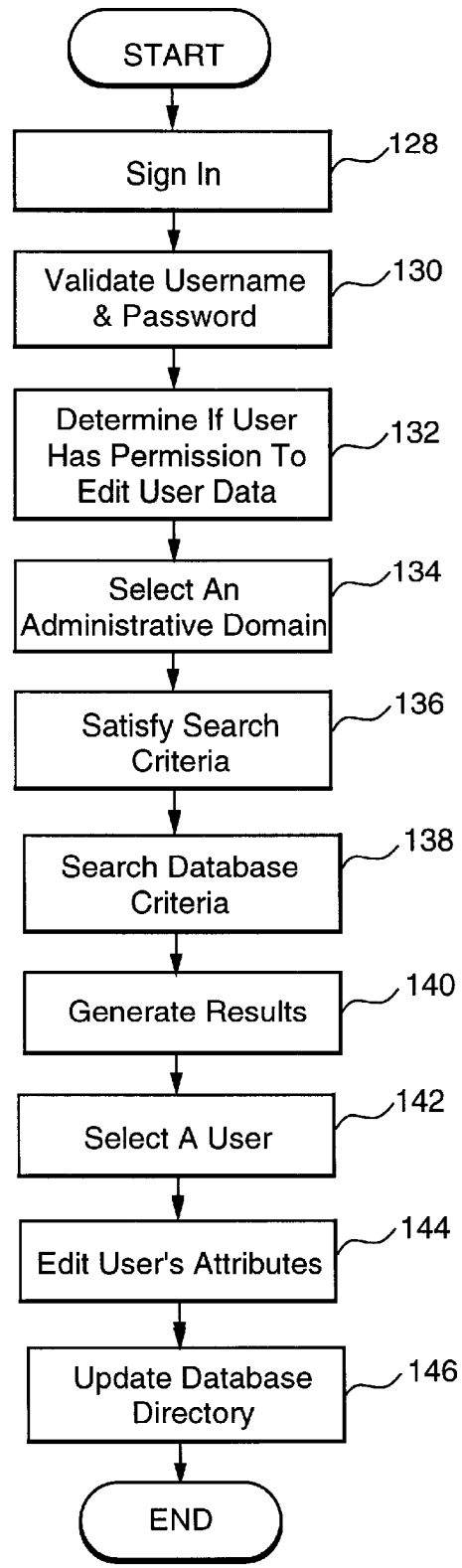
FIG. 11 shows a flow chart describing the acts performed to edit a user's attributes within an administrative domain with the delegated administration tool shown in FIG. 4.

FIG. 11 shows a flow chart describing the acts performed to edit a user's attributes within an administrative domain. The only users that can edit users within an administrative domain are a SuperAdministrator and an administrator having edit authority. If the SuperAdministrator or administrator having edit authority has not already logged onto the delegated administration tool, then he or she must sign in at 128. The delegated administration tool validates the username and password at 130. Alternatively, if the SuperAdministrator or administrator having edit authority has already logged onto the delegated administration tool, then blocks 128–130 may be bypassed. The delegated administration tool then determines if the user has permission (i.e., the user is a SuperAdministrator or administrator with edit authority) to edit a user within an administrative domain at 132. If the user is not authenticated or does not have permission to edit a user within an administrative domain, then the user is not allowed to edit user data within a domain.

At 134, the SuperAdministrator or administrator with edit authority selects a particular administrative domain to search for users therein. At 136, the SuperAdministrator or administrator with edit authority specifies search criteria for searching the database directory from the users in the selected domain. For example, the search criteria could comprise a string for a user, a general description, an attribute, etc. The delegated administration tool parses and interprets the search criteria and searches the database directory according to the criteria at 138. The delegated administration tool parses and formats the search results and presents the results to the user at 140. The SuperAdministrator or administrator with edit authority then selects a single user from the list of users for editing at 142. Then the SuperAdministrator or administrator with edit authority edits the attributes of the user at 144. After the user's attributes have been edited, the database directory is updated at 146 with this data. If the SuperAdministrator or administrator with edit authority wants to edit another user's attributes then blocks 134–146 are repeated. Otherwise, this module can be accessed at a later time.

Figure 12:
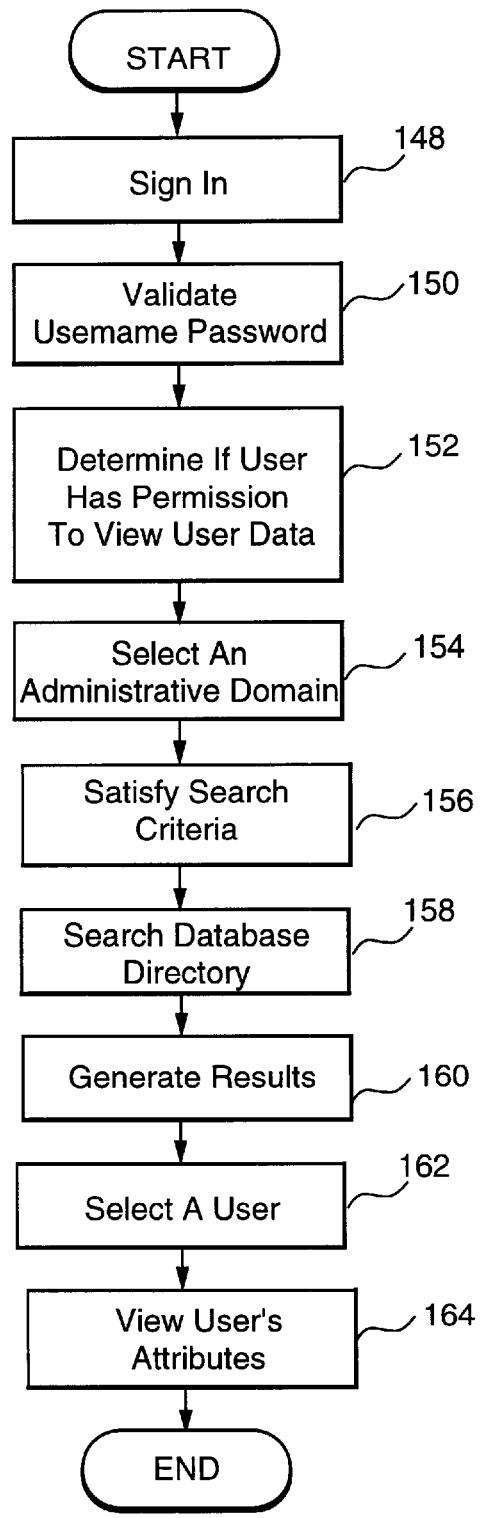
FIG. 12 shows a flow chart describing the acts performed to view a user's attributes within an administrative domain with the delegated administration tool shown in FIG. 4.

FIG. 12 shows a flow chart describing the acts performed to view a user's attributes within an administrative domain. Users that can view user attributes within an administrative domain are a SuperAdministrator, an administrator having delegation authority and an administrator having edit authority. Like the other modules, if the SuperAdministrator or administrator having delegation authority and/or edit authority has not already logged onto the delegated administration tool, then he or she must sign in at 148. The delegated administration tool validates the username and password at 150. Alternatively, if the SuperAdministrator or administrator having delegation authority and/or edit authority has already logged onto the delegated administration tool, then blocks 148–150 may be bypassed. The delegated administration tool then determines if the user has permission (i.e., the user is a SuperAdministrator or administrator with delegation authority and/or edit authority) to view users within an administrative domain at 152. If the user is not authenticated or does not have permission to view users within an administrative domain, then the user is not allowed to view the domain users.

At 154, the SuperAdministrator, administrator with delegation authority or administrator with edit authority selects a particular administrative domain to search for users. At 156, the SuperAdministrator, administrator with delegation authority or administrator with edit authority specifies search criteria for searching the database directory from the users in the specified domain. The delegated administration tool parses and interprets the search criteria and searches the database directory according to the criteria at 158. The delegated administration tool parses and formats the search results and presents a list of users to the user at 160. The SuperAdministrator, administrator with delegation authority or administrator with edit authority then selects a single user from the results for viewing at 162. Then the SuperAdministrator, administrator with delegation authority or administrator with edit authority views the attributes of the user at 164. If the SuperAdministrator, administrator with delegation authority or administrator with edit authority wants to view another user's attributes then blocks 154–164 are repeated. Otherwise, this module can be accessed at a later time.

Figure 13:
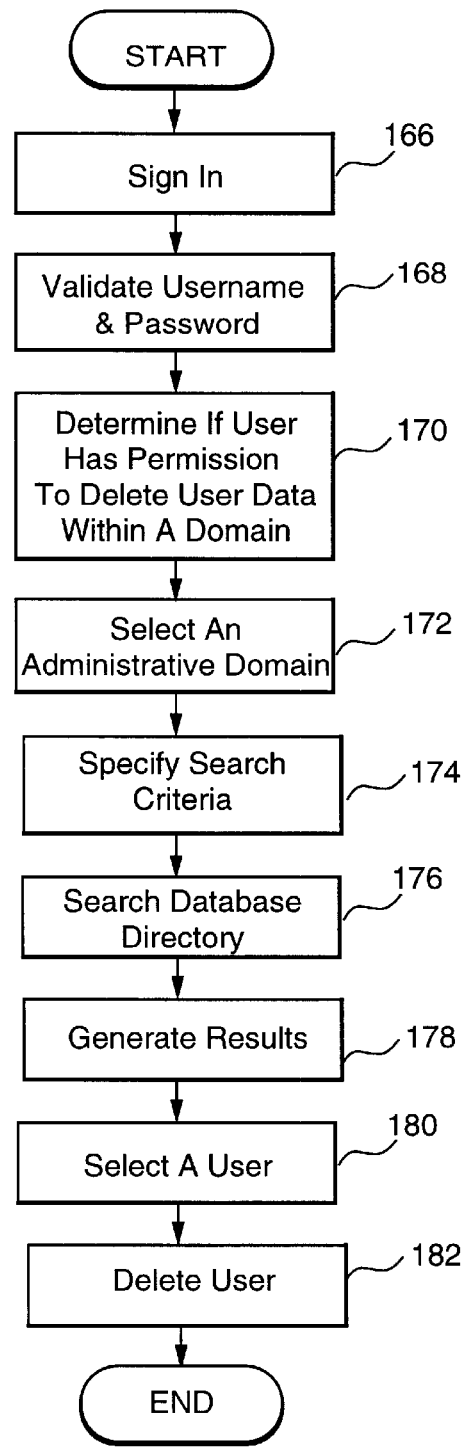
FIG. 13 shows a flow chart describing the acts performed to delete users within an administrative domain with the delegated administration tool shown in FIG. 4.

FIG. 13 shows a flow chart describing the acts performed to delete users within an administrative domain. Users that can delete a user within an administrative domain are a SuperAdministrator and an administrator having edit authority. Like the other modules, if the SuperAdministrator or administrator having edit authority has not already logged onto the delegated administration tool, then he or she must sign in at 166. The delegated administration tool validates the username and password at 168. Alternatively, if the SuperAdministrator or administrator having delegation authority and/or edit authority has already logged onto the delegated administration tool, then blocks 166–168 may be bypassed. The delegated administration tool then determines if the user has permission (i.e., the user is a SuperAdministrator or administrator with edit authority) to delete a user or user attributes from an administrative domain at 170. If the user is not authenticated or does not have permission to delete, then the user is not allowed to do so.

At 172, the SuperAdministrator or administrator with edit authority selects a particular administrative domain to search for users. At 174, the SuperAdministrator or administrator with edit authority specifies search criteria for searching the database directory from the users within the specified domain. The delegated administration tool parses and interprets the search criteria and searches the database directory according to the criteria at 176. The delegated administration tool parses and formats the search results and presents a list of users to the administrator at 178. The SuperAdministrator or administrator with edit authority then selects a single user from the results for deleting at 180. Then the SuperAdministrator or administrator with edit authority deletes the user at 182. If the SuperAdministrator or administrator with edit authority wants to delete another user then blocks 172–182 are repeated. Otherwise, this module can be accessed at a later time.

The foregoing flow charts of this disclosure show the functionality and operation of the delegated administration tool. In this regard, each block represents a module, segment, or portion of code, which comprises one or more executable instructions for implementing the specified logical function(s). It should also be noted that in some alternative implementations, the functions noted in the blocks may occur out of the order noted in the figures or, for example, may in fact be executed substantially concurrently or in the reverse order, depending upon the functionality involved. Also, one of ordinary skill in the art will recognize that additional blocks may be added such as selecting a pertinent administrative domain or changing from one administrative domain to another. Furthermore, the functions can be implemented in programming languages such as C++ or JAVA; however, other languages can be used.

Figure 14B:
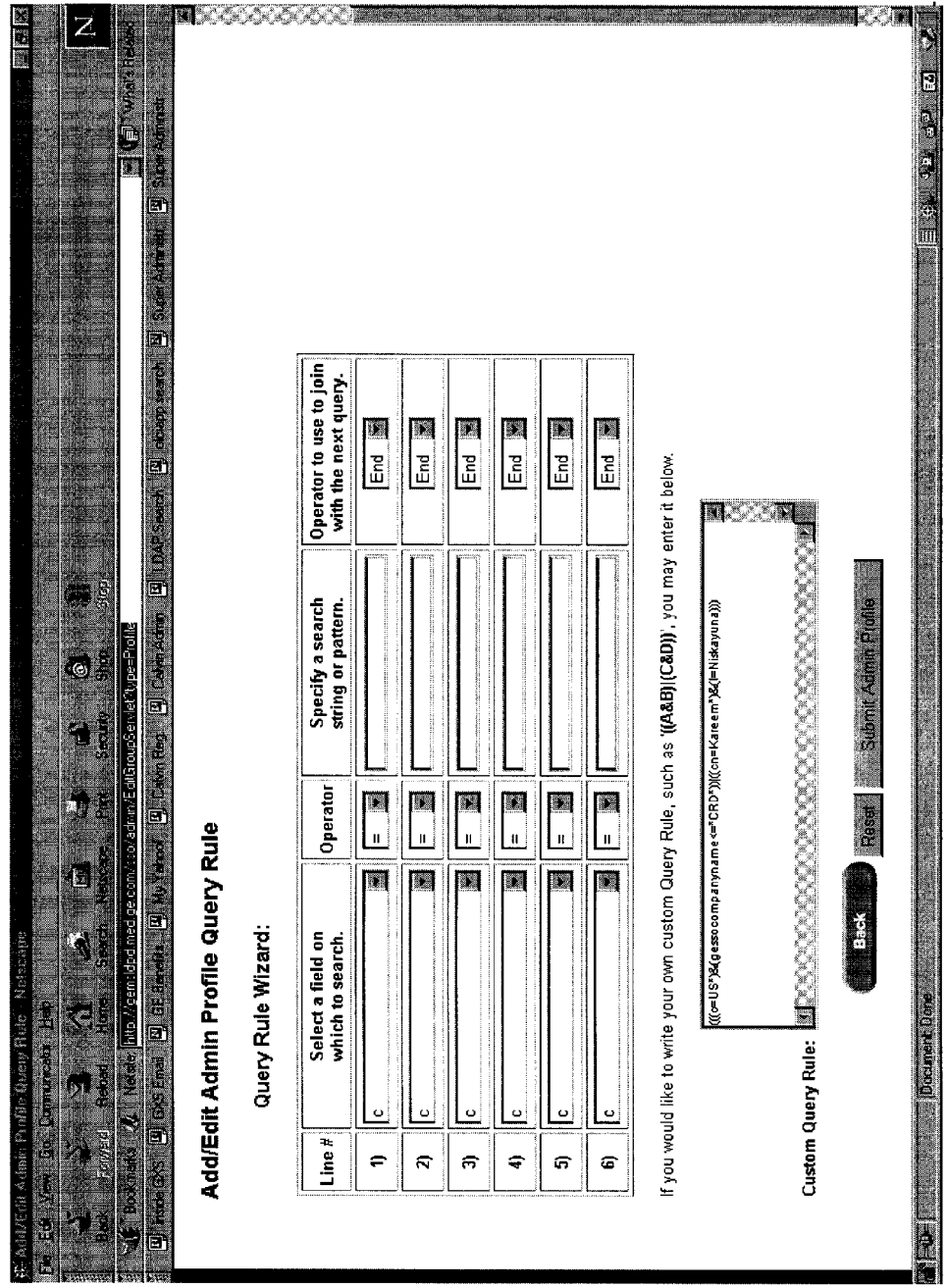

FIGS. 14a–14d show various screen displays that may be presented to a user of the delegated administration tool shown in FIG. 4. These screen displays are for illustrative purposes only and are not exhaustive of other types of displays. Also, the actual look and feel of the displays can be slightly or substantially changed during implementation. FIGS. 14a–14b show screen displays that may be presented to a user after he or she logs into the delegated administration tool 28 and is interested in adding an administrative domain. In particular, FIG. 14a shows a screen display that enables a user to create or edit an administrative domain. In FIG. 14a, the user identifies the administrative domain name and attributes that can be handled for the domain. FIG. 14b shows a screen display that enables a user to construct or edit a query rule for an administrative domain. Each query rule on a line comprises an attribute field for searching, an operator such as "equal to", "less than", "greater than", "less than or equal to", "greater than or equal to", "not equal to", "contains", "does not contain", "excludes", or "does not exclude"; a field for specifying a string or pattern for searching the designated attribute; and another operator such as "AND", or "OR" for coupling this particular query rule to any other rules. One of ordinary skill in the art will recognize that other fields and additional attribute operators can be used to construct a query rule. The screen display in FIG. 14b also presents the user with the option of constructing his or her own custom-made query rule. Constructing a custom-made query rule can be achieved by using Boolean logic, a natural language query or an SQL query.

FIG. 14c shows a screen display that may be presented to a user after he or she logs into the delegated administration tool 28 and is interested in assigning delegation authority and edit authority. In FIG. 14c, the user has selected a particular user for delegating administration and identifies the administrative domain name and the type of authority (i.e., delegation authority and/or edit authority) that the user will have over that domain. In addition, an expiration date for the assigned administrative domain and authority can be designated. As mentioned above, more than one administrative domain can be assigned to a user. Similarly, more than one user may be assigned to a domain. The selections for the domain name, the type of authority and expiration date appear in FIG. 14c as pull-down menus; however, other options for inputting data may be used if desired.

Figure 14D:
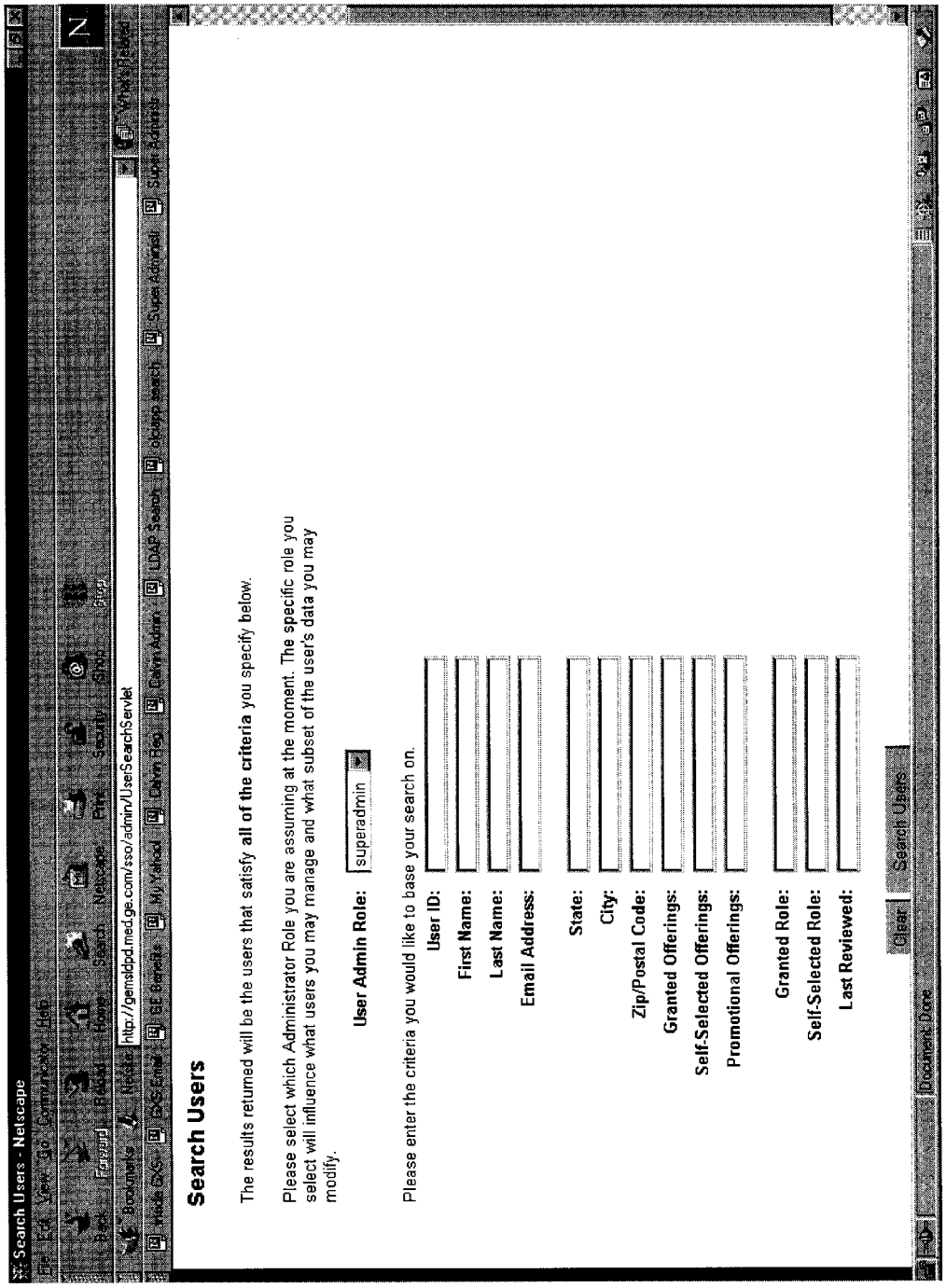

FIG. 14d shows a screen display that may be presented to a user after he or she logs into the delegated administration tool 28 and is interested in editing, viewing or deleting a user or a user's attributes. In FIG. 14d, the user inputs data for a variety of user attributes. The attributes may comprise information such as user identification, name, e-mail address, company, address, resources granted, etc. The delegated administration tool parses and interprets the search criteria and searches the database directory according to the criteria. As mentioned above, the search criteria are applied only to the set of users that satisfy the domain's query rule. The delegated administration tool parses and formats the search results and then presents the results to the user. The user can then perform the edit, view or delete functions.

The above-described delegated administration tool comprises an ordered listing of executable instructions for implementing logical functions. The ordered listing can be embodied in any computer-readable medium for use by or in connection with a computer-based system that can retrieve the instructions and execute them. In the context of this application, the computer-readable medium can be any means that can contain, store, communicate, propagate, transmit or transport the instructions. The computer readable medium can be an electronic, a magnetic, an optical, an electromagnetic, or an infrared system, apparatus, or device. An illustrative, but non-exhaustive list of computer-readable mediums can include an electrical connection (electronic) having one or more wires, a portable computer diskette (magnetic), a random access memory (RAM) (magnetic), a read-only memory (ROM) (magnetic), an erasable programmable read-only memory (EPROM or Flash memory) (magnetic), an optical fiber (optical), and a portable compact disc read-only memory (CDROM) (optical).

Note that the computer readable medium may comprise paper or another suitable medium upon which the instructions are printed. For instance, the instructions can be electronically captured via optical scanning of the paper or other medium, then compiled, interpreted or otherwise processed in a suitable manner if necessary, and then stored in a computer memory.

It is apparent that there has been provided in accordance with this invention, a delegated administration tool. While the invention has been particularly shown and described in conjunction with a preferred embodiment thereof, it will be appreciated that variations and modifications can be effected by a person of ordinary skill in the art without departing from the scope of the invention.

What is claimed is:

1. A method for managing information associated with a user community, comprising:

specifying the information associated with the user community into at least one administrative domain, wherein the at least one administrative domain is a managed object that comprises a set of users, a set of modifiable user attributes and a set of allowable values for the user attributes;

granting administrative privileges for managing the information associated with the user community according to the set of users, attributes and allowable attribute values specified for the at least one administrative domain, wherein the administrative privileges include at least one of delegation authority and edit authority; and specifying the at least one administrative domain into administrative sub-domains each having a set of users, attributes and allowable attribute values and granting administrative privileges for administrating the user community information associated with each sub-domain, wherein the specifying and granting continue to an arbitrary level with respect to the at least one administrative domain.

2. The method according to claim 1, wherein the administrative privileges for administrating the user community information associated with each sub-domain includes at least one of delegation authority and edit authority.

3. The method according to claim 1, further comprising delegating the granted administrative privileges for the at least one administrative domain and administrative sub-domains.

4. A method for providing delegated administration of a user community, comprising:

dividing the user community into at least one administrative domain, wherein the at least one administrative domain is a managed object that comprises a set of users, a set of modifiable user attributes and a set of allowable values for the user attributes;

granting administrative privileges to an administrator for managing user community information according to the set of users, attributes and allowable attribute values specified for the at least one administrative domain, wherein the administrative privileges include at least one of delegation authority and edit authority; and delegating the granted administrative privileges from the administrator to another administrator for managing user community information associated with the at least one administrative domain.

5. The method according to claim 4, further comprising dividing the at least one administrative domain into administrative sub-domains each having a set of users, attributes and allowable attribute values.

6. The method according to claim 5, further comprising delegating the granted administrative privileges to other administrators for managing user community information associated with the administrative sub-domains.

7. The method according to claim 4, further comprising delegating the granted administrative privileges to additional administrators for managing user community information associated with the at least one administrative domain.

8. The method according to claim 4, further comprising dividing the at least one administrative domain into administrative sub-domains each having a set of users, attributes and allowable attribute values and delegating administrative privileges for managing user community information associated with each domain, wherein the dividing and delegating continue to an arbitrary level with respect to the at least one administrative domain.

9. A method for providing delegated administration of a user community with a client system, comprising:

dividing the user community into at least one administrative domain, wherein the at least one administrative domain is a managed object that comprises a set of users, a set of modifiable user attributes and a set of allowable values for the user attributes;

granting administrative privileges to an administrator for managing user community information according to the set of users, attributes and allowable attribute values specified for the at least one administrative domain, wherein the administrative privileges include at least one of delegation authority and edit authority;

dividing the at least one administrative domain into administrative sub-domains each having set of users, attributes and allowable attribute values; and delegating the granted administrative privileges from the administrator to other administrators for managing user community information associated with the administrative sub-domains.

10. The method according to claim 9, further comprising dividing the administrative sub-domains into more domains each having a set of users, attributes and allowable attribute values and delegating administrative privileges for managing user community information associated with each of these domains, wherein the dividing and delegating continue to an arbitrary level with respect to the at least one administrative domain.

11. The method according to claim 9, wherein the delegating of granted administrative privileges comprises having an administrator with delegation authority delegating at least one of delegation authority and edit authority and an administrator with edit authority delegating edit authority.

12. A method for enabling an administrator to control administration of information associated with a user community, comprising:

providing the information associated with the user community to the administrator;

prompting the administrator to define at least one administrative domain for the user community, wherein the at least one administrative domain is a managed object that comprises a set of users, a set of modifiable user attributes and a set of allowable values for the user attributes;

prompting the administrator to define administrative privileges for managing user community information according to the set of users, attributes and allowable attribute values defined for the at least one administrative domain, wherein the administrative privileges include at least one of delegation authority and edit authority; and using the at least one administrative domain and administrative privileges defined by the administrator to control administration of the information associated with the user community.

13. The method according to claim 12, further comprising prompting the administrator to divide the at least one administrative domain into administrative sub-domains each having a set of users, attributes and allowable attribute values.

14. The method according to claim 13, further comprising prompting the administrator to delegate the granted administrative privileges from the administrator to other administrators for the administrative sub-domains.

15. The method according to claim 14, further comprising prompting the administrator to divide the administrative sub-domains into more domains each having a set of users, attributes and allowable attribute values and delegate administrative privileges for managing user community information associated with each of these domains, wherein the prompting to divide and delegate continues to an arbitrary level with respect to the at least one administrative domain.

16. A method for enabling an administrator to delegate administrative control of a user community, comprising:

providing information associated with the user community;

prompting the administrator to define at least one administrative domain for the user community, wherein the at least one administrative domain is a managed object that comprises a set of users, a set of modifiable user attributes and a set of allowable values for the user attributes;

prompting the administrator to define administrative privileges for managing user community information according to the set of users, attributes and allowable attribute values defined for the at least one administrative domain, wherein the administrative privileges include at least one of delegation authority and edit authority;

prompting the administrator to divide the at least one administrative domain into administrative sub-domains each having a set of users, attributes and allowable attribute values;

prompting the administrator to delegate the granted administrative privileges from the administrator to other administrators for managing user community information associated with the administrative sub-domains; and using the administrative domains and administrative privileges to control administration of the information associated with the user community.

17. A user community administration tool for managing information associated with a user community, comprising:
- a domain definition component that defines the user community into at least one administrative domain, wherein the at least one administrative domain is a managed object that comprises a set of users, a set of modifiable user attributes and a set of allowable values for the user attributes;
- an administrative privileges component that grants administrative privileges for managing user community information according to the set of users, attributes and allowable attribute values defined for the at least one administrative domain, wherein the administrative privileges include at least one of delegation authority and edit authority; and
- an information management component that manages user community information associated with the at least one administrative domain in accordance with the granted administrative privileges.

18. The tool according to claim 17, wherein the domain definition component specifies the at least one administrative domain into administrative sub-domains each having a set of users, attributes and allowable attribute values.

19. The tool according to claim 18, wherein the administrative privileges component delegates the administrative privileges for managing user community information associated with the administrative sub-domains.

20. The tool according to claim 17, wherein the administrative privileges component delegates the granted administrative privileges for managing user community information associated with the at least one administrative domain.

21. The tool according to claim 17, wherein the domain definition component specifies administrative sub-domains each having a set of users, attributes and allowable attribute values and the administrative privileges component delegates the administrative privileges for managing user community information associated with the domains to an arbitrary level with respect to the at least one administrative domain.

22. A system for managing information associated with a user community, comprising:
- a database directory containing a plurality of user information;
- a user community administration tool to manage the plurality of user information in the database directory; the user community administration tool comprising a domain definition component to define the user community into at least one administrative domain, wherein the at least one administrative domain is a managed object that comprises a set of users, a set of modifiable user attributes and a set of allowable values for the user attributes; an administrative privileges component to grant administrative privileges for managing user community information according to the set of users, attributes and allowable attribute values defined for the at least one administrative domain, wherein the administrative privileges include at least one of delegation authority and edit authority; and an information management component to manage user community information associated with the at least one administrative domain in accordance with the granted administrative privileges; and
- a first computing unit configured to serve the user community administration tool and the database directory.

23. The system according to claim 22, wherein the domain definition component specifies the at least one administrative domain into administrative sub-domains each having a set of users, attributes and allowable attribute values.

24. The system according to claim 23, wherein the administrative privileges component delegates the administrative privileges for managing user community information associated with the administrative sub-domains.

25. The system according to claim 22, wherein the administrative privileges component delegates the granted administrative privileges for managing user community information associated with the at least one administrative domain.

26. The system according to claim 22, further comprising a second computing unit configured to execute the user community administration tool served from the first computing unit over a network.

27. A system for managing information associated with a user community, comprising:
- a database directory containing a plurality of user information;
- a user community administration tool to manage the plurality of user information in the database directory; the user community administration tool comprising a domain definition component to define the user community into at least one administrative domain, wherein the at least one administrative domain is a managed object that comprises a set of users, a set of modifiable user attributes and a set of allowable values for the user attributes; an administrative privileges component to grant administrative privileges for managing user community information according to the set of users, attributes and allowable attribute values defined for the at least one administrative domain, wherein the administrative privileges include at least one of delegation authority and edit authority; and an information management component to manage user community information associated with the at least one administrative domain in accordance with the granted administrative privileges;
- a first computing unit configured to execute the user community administration tool;
- a network; and
- a second computing unit configured to serve the database directory and the user community administration tool to the first computing unit over the network.

28. A user community administration tool for providing delegated administration of a user community, comprising:
- means for dividing the user community into at least one administrative domain, wherein the at least one administrative domain is a managed object that comprises a set of users, a set of modifiable user attributes and a set of allowable values for the user attributes;
- means for granting administrative privileges to an administrator for managing user community information according to the set of users, attributes and allowable attribute values specified for the at least one administrative domain, wherein the administrative privileges include at least one of delegation authority and edit authority; and
- means for delegating the granted administrative privileges to another administrator for managing user community information associated with the at least one administrative domain.

29. The tool according to claim 28, further comprising means for dividing the at least one administrative domain into administrative sub-domains each having a set of users, attributes and allowable attribute values.

30. The tool according to claim 29, further comprising means for delegating the granted administrative privileges to other administrators for managing user community information associated with the administrative sub-domains, wherein an administrator with delegation authority delegates at least one of delegation authority and edit authority, while an administrator with edit authority delegates edit authority.

31. The tool according to claim 28, further comprising means for delegating the granted administrative privileges to additional administrators for managing user community information associated with the at least one administrative domain.

32. A system for providing delegated administrative control of a user community, comprising:
 a database directory containing a plurality of user information associated with the user community: and
 a user community administration tool to facilitate administrative control of the user information in the database directory; the user community administration tool comprising a domain definition component to define the user community into at least one administrative domain, wherein the at least one administrative domain is a managed object that comprises a set of users, a set of modifiable user attributes and a set of allowable values for the user attributes; an administrative privileges component to grant administrative privileges for managing user community information according to the set of users, attributes and allowable attribute values defined for the at least one administrative domain, wherein the administrative privileges include at least one of delegation authority and edit authority; and an information management component to manage user community information associated with the at least one administrative domain in accordance with the granted administrative privileges.

33. The system according to claim 32, wherein the domain definition component divides the at least one administrative domain into administrative sub-domains each having a set of users, attributes and allowable attribute values.

34. The system according to claim 33, wherein the administrative privileges component delegates the administrative privileges to an arbitrary level of administrators for managing user community information associated with the administrative sub-domains.

35. The system according to claim 32, wherein the administrative privileges component delegates the granted administrative privileges from the administrator to other administrators for managing user community information associated with the at least one administrative domain.

36. A computer-readable medium storing computer instructions for instructing a computer system to provide delegated administration of a user community, the computer instructions comprising:
 dividing the user community into at least one administrative domain, wherein the at least one administrative domain is a managed object that comprises a set of users, a set of modifiable user attributes and a set of allowable values for the user attributes;
 granting administrative privileges to an administrator for managing user community information according to the set of users, attributes and allowable attribute values defined for the at least one administrative domain, wherein the administrative privileges include at least one of delegation authority and edit authority; and
 delegating the granted administrative privileges to another administrator for managing user community information associated with the at least one administrative domain.

37. The computer-readable medium according to claim 36, further comprising instructions for dividing the at least one administrative domain into administrative sub-domains each having a set of users, attributes and allowable attribute values.

38. The computer-readable medium according to claim 37, further comprising instructions for delegating the granted administrative privileges to other administrators for managing user community information associated with the administrative sub-domains.

39. The computer-readable medium according to claim 36, further comprising instructions for delegating the granted administrative privileges to additional administrators for managing user community information associated with the at least one administrative domain.

40. The computer-readable medium according to claim 36, further comprising instructions for dividing the at least one administrative domain into administrative sub-domains each having a set of users, attributes and allowable attribute values and delegating administrative privileges for managing user community information associated with each domain, wherein the dividing and delegating continue to an arbitrary level with respect to the at least one administrative domain.

41. The computer-readable medium according to claim 36, further comprising instructions for managing user community information associated with the at least one administrative domain according to the delegated administrative privileges.

42. A computer-readable medium storing computer instructions for instructing a computer system to provide delegated administration of a user community, the computer instructions comprising:
 dividing the user community into at least one administrative domain, wherein the at least one administrative domain is a managed object that comprises a set of users, a set of modifiable user attributes and a set of allowable values for the user attributes;
 granting administrative privileges to an administrator for managing user community information according to the set of users, attributes and allowable attribute values defined for the at least one administrative domain, wherein the administrative privileges include at least one of delegation authority and edit authority;
 dividing the at least one administrative domain into administrative sub-domains each having a set of users, attributes and allowable attribute values; and
 delegating the granted administrative privileges from the administrator to other administrators for managing user community information associated with the administrative sub-domains.

43. The computer-readable medium according to claim 42, further comprising instructions for dividing the administrative sub-domains into more domains each having a set of users, attributes and allowable attribute values and delegating administrative privileges for managing user community information associated with each of these domains, wherein the dividing and delegating continue to an arbitrary level with respect to the at least one administrative domain.

44. A computer-readable medium storing computer instructions for instructing a computer system to enable an administrator to control administration of a user community, the computer instructions comprising:
 providing information associated with the user community to the administrator;
 prompting the administrator to define at least one administrative domain for the user community, wherein the at least one administrative domain is a managed object that comprises a set of users, a set of modifiable user attributes and a set of allowable values for the user attributes;

prompting the administrator to define administrative privileges for managing user community information according to the set of users, attributes and allowable attribute values defined for the at least one administrative domain, wherein the administrative privileges include at least one of delegation authority and edit authority; and using the at least one administrative domain and administrative privileges defined by the administrator to control administration of the information associated with the user community.

45. The computer-readable medium according to claim 44, further comprising instructions for prompting the administrator to divide the at least one administrative domain into administrative sub-domains each having a set of users, attributes and allowable attribute values.

46. The computer-readable medium according to claim 45, further comprising instructions for prompting the administrator to delegate the granted administrative privileges from the administrator to other administrators for managing user community information associated with the administrative sub-domains.

47. The computer-readable medium according to claim 46, further comprising instructions for prompting the administrator to divide the administrative sub-domains into more domains each having a set of users, attributes and allowable attribute values and delegate administrative privileges for managing user community information associated with each of these domains, wherein the prompting to divide and delegate continues to an arbitrary level with respect to the at least one administrative domain.

48. A computer-readable medium containing computer instructions for instructing a computer system to enable an administrator to delegate administration control of a user community, the computer instructions comprising:

providing information associated with the user community;

prompting the administrator to define at least one administrative domain for the user community, wherein the at least one administrative domain is a managed object that comprises a set of users, a set of modifiable user attributes and a set of allowable values for the user attributes;

prompting the administrator to define administrative privileges for managing user community information according to the set of users, attributes and allowable attribute values defined for the at least one administrative domain, wherein the administrative privileges include at least one of delegation authority and edit authority;

prompting the administrator to divide the at least one administrative domain into administrative sub-domains each having a set of users, attributes and allowable attribute values;

prompting the administrator to delegate the granted administrative privileges from the administrator to other administrators for managing user community information associated with the administrative sub-domains; and using the at least one administrative domain and administrative sub-domains and administrative privileges and delegated privileges defined by the administrator to control administration of the information associated with the user community.

* * * * *